US010668467B2

(12) United States Patent
Vanapalli et al.

(10) Patent No.: US 10,668,467 B2
(45) Date of Patent: Jun. 2, 2020

(54) MICROFLUIDIC DEVICE FOR STUDYING NEMATODES

(71) Applicant: Texas Tech University System, Lubbock, TX (US)

(72) Inventors: Siva A. Vanapalli, Lubbock, TX (US); Mizanur Rahman, Lalmonirhat (BD)

(73) Assignee: Texas Tech University System, Lubbock, TX (US)

(*) Notice: Subject to any disclaimer, the term of this patent is extended or adjusted under 35 U.S.C. 154(b) by 235 days.

(21) Appl. No.: 15/580,318

(22) PCT Filed: Jun. 7, 2016

(86) PCT No.: PCT/US2016/036131
§ 371 (c)(1),
(2) Date: Dec. 7, 2017

(87) PCT Pub. No.: WO2016/200758
PCT Pub. Date: Dec. 15, 2016

(65) Prior Publication Data
US 2018/0161771 A1  Jun. 14, 2018

Related U.S. Application Data

(60) Provisional application No. 62/173,888, filed on Jun. 10, 2015.

(51) Int. Cl.
*G01N 1/18* (2006.01)
*B01L 3/00* (2006.01)
(Continued)

(52) U.S. Cl.
CPC ............ *B01L 3/5027* (2013.01); *G01N 33/48* (2013.01); *B01L 2300/0816* (2013.01); *B01L 2400/086* (2013.01)

(58) Field of Classification Search
CPC ....... B01L 2300/0816; B01L 2400/086; B01L 3/5027; G01N 33/48
See application file for complete search history.

(56) References Cited

U.S. PATENT DOCUMENTS 8,592,221 B2  11/2013  Fraden et al.
8,702,939 B2  11/2014  Selvaganapathy et al.
(Continued)

FOREIGN PATENT DOCUMENTS

WO  2014116183 A1  7/2014
WO  2014207257 A1  12/2014

OTHER PUBLICATIONS

Ai, X. et al. "A high-throughput device for size based separation of C. elegans developmental stages", Lab on a Chip, May 21, 2014, 14(10), pp. 1746-1752.
(Continued)

*Primary Examiner* — Jennifer Wecker
(74) *Attorney, Agent, or Firm* — Daniel J. Chalker; Edwin S. Flores; Chalker Flores, LLP

(57) ABSTRACT

A microfluidic device includes a substrate, a cover layer and one or more chambers disposed within the cover layer, the substrate or both. Each chamber has a first end, a second end, and a set of micro-pillars disposed therein. A first microchannel and second microchannel are disposed within the cover layer, the substrate or both, and connected to the first end and second end of the chamber, respectively. A first set of barriers is disposed within each first microchannel proximate to the first end of the chamber. A second set of barriers is disposed within each second microchannel proximate to the second end of the chamber. A third microchannel is disposed within the cover layer, the substrate or both, and connected to the chamber. A first port, second port and third
(Continued)

port extend through the cover layer and connect to the first, second and third microchannels, respectively.

32 Claims, 13 Drawing Sheets

(51) Int. Cl.
*C12M 3/00* (2006.01)
*G01N 33/48* (2006.01)

(56) References Cited

U.S. PATENT DOCUMENTS

| | | | |
|---|---|---|---|
| 2010/0216241 A1* | 8/2010 | Yu | C12M 25/06 435/395 |
| 2010/0263599 A1* | 10/2010 | Yanik | A61K 49/0008 119/216 |
| 2013/0309679 A1* | 11/2013 | Ismagilov | C12N 15/1003 435/6.12 |
| 2014/0051062 A1 | 2/2014 | Vanapalli et al. | |
| 2014/0057339 A1* | 2/2014 | Esfandyarpour | G01N 27/327 435/287.2 |
| 2014/0154703 A1* | 6/2014 | Skelley | B01L 3/502761 435/7.23 |
| 2016/0016169 A1* | 1/2016 | Ben-Yakar | B01L 3/502738 506/26 |
| 2016/0136642 A1* | 5/2016 | Eriksen | B01L 3/502715 435/6.12 |

OTHER PUBLICATIONS

Johari, S. et al., "High-Throughput Microfluidic Sorting of C. elegans for Automated Force Pattern Measurement", Materials Science Forum, 2012, vol. 700, pp. 182-187.
International Search Report [PCT/US2016/036131] (AU/RO) dated Aug. 31, 2016.

* cited by examiner

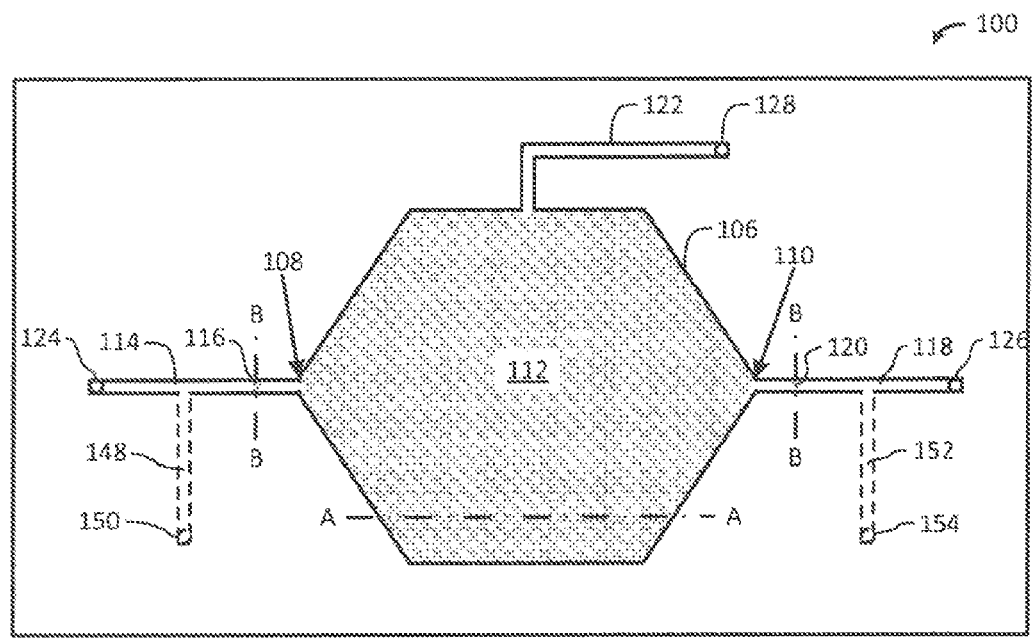
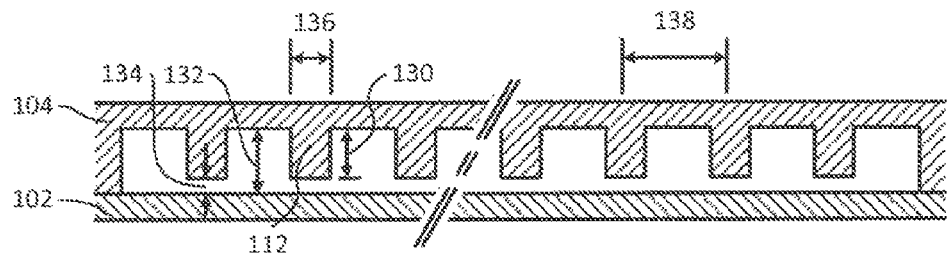
Section A - A
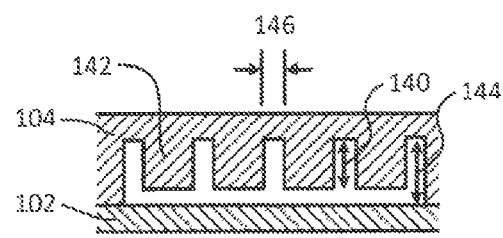
Section B - B
FIG. 1

| FEEDING FREQUENCY (SPACING 40/60 μm/μm) | FOOD CONCENTRATION | | | | |
|---|---|---|---|---|---|
| | 100 mg/mL | | 200 mg/mL | | |
| | MEDIAN LIFESPAN | MAX LIFESPAN | MEDIAN LIFESPAN | MAX LIFESPAN | |
| TWICE/DAY | 15 | 23 | - | - | |
| ONCE/DAY | 16 | 20 | 16 | 21 | |
| EVERY OTHER DAY | 13 | 27 | - | - | |

| | | FOOD CONCENTRATION: 100 mg/mL | |
|---|---|---|---|
| | SPACING μm/μm | ONCE/DAY | |
| | | MEDIAN LIFESPAN | MAX LIFESPAN |
| | 40/60 | 16 | 23 |
| | 50/80 | 15 | 22 |
| | 60/100 | 17 | 23 |

| FEEDING FREQUENCY (ONCE/DAY) | TRIAL 1 | | | TRIAL 2 | | | TRIAL 3 | | |
|---|---|---|---|---|---|---|---|---|---|
| | MEDIAN LIFESPAN | MAX LIFESPAN | n | MEDIAN LIFESPAN | MAX LIFESPAN | n | MEDIAN LIFESPAN | MAX LIFESPAN | n |
| WILD TYPE | 17 | 24 | 80 | 14 | 25 | 163 | 15 | 25 | 128 |
| age-1(hx546) | 20 | 33 | 167 | 21 | 37 | 152 | | | |
| daf-16(ngDf50) | 15 | 22 | 163 | | | | | | |
| daf-2(DR1564) | 18 | 31 | 160 | | | | | | |
| daf-2(e1370) | 28 | 44 | | | | | | | |

FOOD CONCENTRATION: 100 mg/mL
DEVICE SPACING: 60/100 μm/μm

FIG. 8

| Device with pillar geometry diameter μm/spacing μm | Ratio of Spacing/diameter | Wavelength λ μm | | Amplitude σ μm | |
|---|---|---|---|---|---|
| | | mean | SD | mean | SD |
| 40/60 | 1.2 ≥ R₁ ≥ 0.68 | 543.9 | 63.8 | 266.4 | 83.1 |
| 50/80 | 1.6 ≥ R₂ ≥ 0.90 | 530.2 | 33.4 | 149.1 | 57.8 |
| 60/100 | 2.0 ≥ R₃ ≥ 1.15 | 606.9 | 53.4 | 197.3 | 34.6 |
| Agar* | - | 650 | 40 | - | - |

FIG. 9

MICROFLUIDIC DEVICE FOR STUDYING NEMATODES

CROSS-REFERENCE TO RELATED APPLICATIONS

This application is the National Stage of International Application No. PCT/US2016/036131, filed on Jun. 7, 2016, which claims priority to U.S. Provisional Patent Application Ser. No. 62/173,888, filed on Jun. 10, 2015. The contents of both applications are incorporated by reference herein in their entirety.

STATEMENT OF FEDERALLY FUNDED RESEARCH

This invention was made with U.S. Government support awarded by NSF grant number 1150836. The government has certain rights in this invention.

FIELD OF THE INVENTION

The present invention relates generally to the field of microfluidics, and more particularly to a microfluidic device for studying nematodes.

BACKGROUND OF THE INVENTION

Aging pushes an active and jubilant life into a sloth and sometimes miserably bed-ridden life. Aged adult's experiences age-associated diseases and loss of functionality. However, healthy aging is also observed within individuals who normally have active life throughout. An understanding of the underlying genetics of healthy aging may significantly improve human health. The essential question to this problem is (i) how tissues and organs age and (ii) what determines the lifespan? To elucidate the puzzle, specific response to molecular, environmental or genetic perturbation is observed throughout the lifespan of the animal. Utilizing the process, molecular biologists identified age-regulating signaling pathways such as insulin/insulin like growth factor (IGF-1), target of rapamycin, AMP kinase and signaling through sirtuins. These pathways alternatively are specific to their environmental and physiological stresses. In last two decades, more than hundred lifespan influencing genetic mutations have been discovered. These suggest, lifespan is a complex interaction of environmental factors and genetic. Hence, effect of any or combination of perturbation can be observed only through the lifespan of a population and lifespan study remains the core of aging research.

In addition, maintenance of muscle strength is essential for an individual's health and well being. In fact, loss of muscle strength is a prognostic indicator for a variety of disorders including sarcopenia, cancer, and neuromuscular diseases. Decline in muscle strength is also a significant issue for space explorers. Therefore, a major challenge for muscle health research is to understand the genetic mechanisms regulating strength.

*Caenorhabditis elegans* (*C. elegans*) is an established model organism for aging research. In addition, the *C. elegans* body wall muscles have similarities to the human muscle and also deteriorate with age much like in humans. Thus, prospective life-long muscle health studies can be accomplished in the roundworm *C. elegans*. It has a short lifespan of 3-5 weeks which allows observing the effects of genetic modification on the animal's lifespan in a relative short time period.

It is genetically tractable. Green fluorescent protein (GFP) tagging in the transparent body makes it ideal for observing age-related physiological and biochemical changes through the lifespan. Generally, *C. elegans* is cultured in bacteria lawn grown on agar plate and completes it's life cycle in 3 days. Predominantly, lifespan study is carried out on agar plate by manually transferring the adult worms periodically in new plates. Tedious agar plate based lifespan study severely limits the number of animals per experiment and number of experiments that can be carried out at a given time. This makes the timescale of a complete hypothesis test on the order of year. In addition to that, there are issues of loss of animal during study and contamination with bacteria/fungi. Variation in temperature, moisture/evaporation and quality of food contributes in lab-to-lab variation of lifespan. However, it is even more tedious and time intensive in case of any drug assay on lifespan due to the fact of diffusion limitation. Addition and withdrawal of drug/chemo-attractant has the same limitation of transferring the worms in new plates.

In agar plate, worms crawl by undulating their body sinusoidally in smooth surface. Generally, moisture from agar surface creates meniscus all along the body of the worm and capillary action actually pins the worm on agar surface. Worms have to continuously break the contact line and renew. Also, slips on the agar surface force the worm to work more. In its natural environment there are pores in the soil and some are connected. So, they feel the support of random size from all side of their body and can use the pores/walls of pores to support their crawling movement. It is likely that they will face lots of obstacles on their way as the pores have turns and dead ends. Naturally, head will forage a lot, touch sensory neurons will function constantly and muscles will be working all along the body for making the way out. It is now established that environmental stresses influence *C. elegans* lifespan to a considerable extent. In short, the environmental stresses in their natural environment are probably very different than in agar plate and probably result in underestimation of *C. elegans* lifespan.

A few attempts have been made recently to demonstrate liquid based lifespan devices. Most of them focused on reducing the manual intervention of transferring, prodding and scoring. A microfluidic chamber based device has been reported for the lifespan study in which worms were maintained in unobstructed circular chambers filled with liquid media and progeny was separated by inducing flow through a narrow channel allowing only the progeny to flow out of the chamber. The lifespan was reported to be 8-10 days at 24° C. for wild type animals based on 16 animals assay. A 96 well microtiter plate based lifespan study has also been reported in which the contamination with progeny was eliminated by using the drug 2'-deoxy-5-fluorouridine (Floxuridine, FUdR) to prevent hatching of eggs. Most recently, a microfluidic lifespan device (WormFarm) has been reported integrated with automated feeding and image analysis features in which a series of small channels connected to each side of the device was used as screen to separate progeny from the adult worms. A mean lifespan of 8.68 days (max lifespan 14 day) for wild type and 13 days (max lifespan 24 days) for age-1 was reported at 25° C. based on 200-400 animals. In all of the above techniques *C. elegans* are allowed to swim all through their life in their food environment. Worms maintaining swim gait throughout their life may experience stresses of unknown effect on their lifespan. It is also demonstrated that excessive swimming is detrimental for worm health. Use of drug FUdR reportedly has influence on *C. elegans* lifespan. Addition of valves in the microfluidic chip, requirement of pumps, interfaces for controlling fluid delivery to the device and software for image processing may limit a microfluidic lifespan device for easy, fast and bench-top use for a biologist. Around the same time, a capital intensive lifespan machine was reported which is a scanner based technology and can handle large population of worms in an experiment. A lifespan machine is capable of capture images and analyze lifespan automatically. However, it is still agar based assay and poses all the limitations of agar based lifespan scoring.

SUMMARY OF THE INVENTION

The present invention provides a fast and simple to use lifespan assay system that speeds up aging experiments with more control. The microfluidic device can used to efficiently measure lifespan and healthspan of *C. elegans* and its genetic mutants, without requiring drug blocking of progeny production. The geometry of the microfluidic device allows the removal of progeny while efficiently retaining the adult worms in the device. In addition, the geometry of the microfluidic device and feeding protocols provide worm gait, body size, and lifespan that are consistent with standard aging assays on agar. Moreover, the small footprint of the device combined with unprecedented capacity to add or remove reagents at any time point in the lifespan, enables highly parallelized and novel cross-sectional and longitudinal aging experiments.

One embodiment of the present invention provides a microfluidic device that includes a substrate, a cover layer attached to the substrate and one or more chambers disposed within the cover layer, the substrate or both. Each chamber has a first end, a second end, and a set of micro-pillars disposed within the chamber. A first microchannel is disposed within the cover layer, the substrate or both, and connected to the first end of the chamber. A first set of barriers is disposed within each first microchannel proximate to the first end of the chamber. A second microchannel is disposed within the cover layer, the substrate or both, and connected to the second end of the chamber. A second set of barriers is disposed within each second microchannel proximate to the second end of the chamber. A third microchannel is disposed within the cover layer, the substrate or both, and connected to the chamber. A first port (e.g., buffer exchange/feeding/drug loading port) extends through the cover layer and connects to the first microchannel. A second port (e.g., buffer exchange/feeding/drug loading port) extends through the cover layer and connects to the second microchannel. A third port (e.g., worm inlet port) extends through the cover layer and connects to the third microchannel.

Another embodiment of the present invention provides a method of making a microfluidic device having one or more chambers in accordance with one embodiment of the present invention is shown. A cover layer is formed. For each chamber, the cover layer includes a cavity with a first end and a second end, a set of micro-pillars disposed within the cavity, a first microchannel connected to the first end of the cavity, a first set of barriers disposed within the first microchannel proximate to the first end of the cavity, a second microchannel connected to the second end of the cavity, a second set of barriers disposed within the second microchannel proximate to the second end of the cavity, and a third microchannel connected to the cavity. For each chamber, a first port, a second port and a third port are formed through the cover layer. The first port is connected to the first microchannel, the second port is connected to the second microchannel, and the third port is connected to the third microchannel. The cover layer is attached to a substrate such that each cavity forms one of the chambers, and the first microchannel, the second microchannel and the third microchannel are enclosed.

Yet another embodiment of the present invention provides a method for measuring a lifespan or a muscular strength or both of worms. A microfluidic device is provided, which includes a substrate, a cover layer attached to the substrate, one or more chambers disposed within the cover layer, the substrate or both, wherein each chamber has a first end and a second end, a set of micro-pillars disposed within each chamber. Each chamber further includes a first microchannel disposed within the cover layer, the substrate or both, and connected to the first end of the chamber, a first set of barriers disposed within each first microchannel proximate to the first end of the chamber, a second microchannel disposed within the cover layer, the substrate or both, and connected to the second end of the chamber, a second set of barriers disposed within each second microchannel proximate to the second end of the chamber, a third microchannel disposed within the cover layer, the substrate or both, and connected to the chamber, a first port extending through the cover layer and connected to the first microchannel, a second port extending through the cover layer and connected to the second microchannel, and a third port extending through the cover layer and connected to the third microchannel. The worms are introduced into the chamber via the third port using a pipette. A food, a buffer or a drug are periodically introduced into the chamber via the first port or the second port using the pipette. The lifespan or the muscular strength or both of the worms within the chamber are measured.

The present invention is described in detail below with reference to the accompanying drawings.

DESCRIPTION OF THE DRAWINGS

The above and further advantages of the invention may be better understood by referring to the following description in conjunction with the accompanying drawings, in which:

FIG. 1 is a block diagram of microfluidic device in accordance with one embodiment of the present invention;

FIG. 8 shows tables for lifespan study (development of feeding protocol, spacing trials, reproducibility of lifespan for the wild type animal in optimized device with optimized diet, and lifespan for age mutants) in accordance with one embodiment of the present invention; and FIG. 9 is a table showing a characterization of crawling behavior of worms in fluidic micropillar arena in accordance with one embodiment of the present invention.

DESCRIPTION OF THE INVENTION

Figure 2:
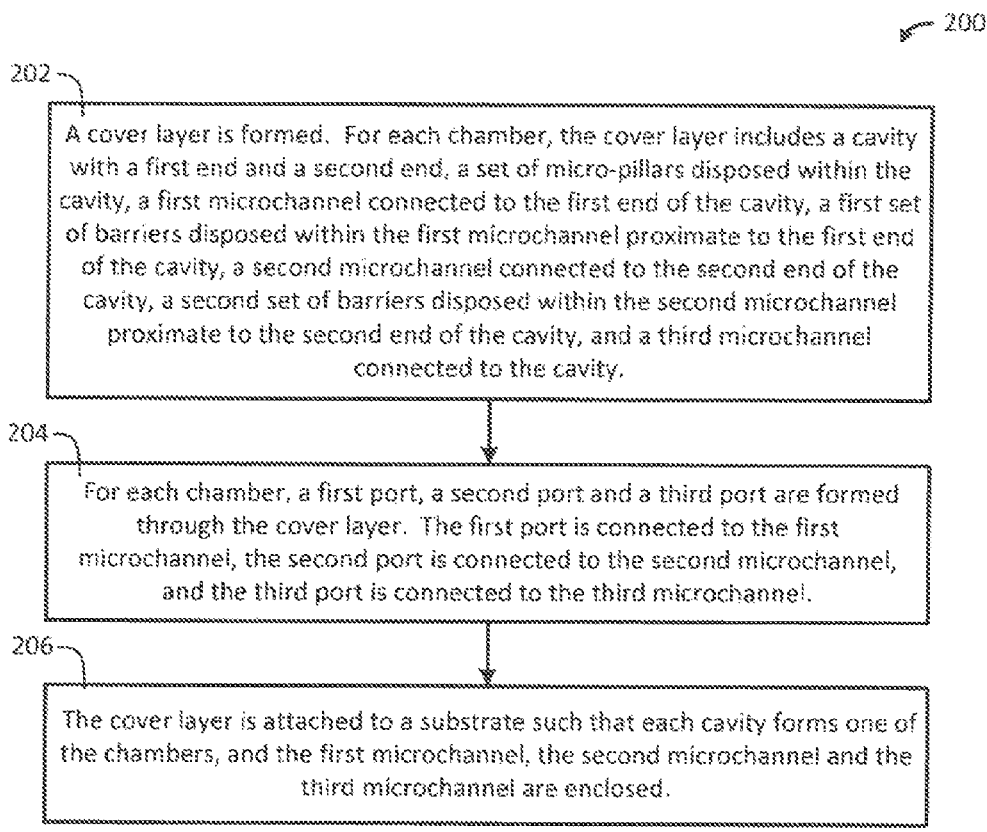
FIG. 2 is a flow chart of a method of making a microfluidic device having one or more chambers in accordance with one embodiment of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

The present invention will be described in reference to a non-limiting embodiment in which a microfluidic device has one or more chambers containing regularly spaced deformable micro-pillars for *C. elegans* lifespan and muscular strength study. The regularly spaced deformable micro-pillars are a closer match to their natural environment and forces the worms to adopt crawling gait. Optimized micro-pillar spacing ensures worm locomotion as in the agar plate. Instead of a bacterial lawn in agar habitat, this device uses liquid media. The device is optimized for hand pipetting and easy to use bench-top device requiring no additional equipment and supply. As a result, loading, synchronization, washing, feeding, and data acquisition are no longer tedious. Thus, parallelization is simple and the device is flexible in the number of animals/experiment, the number of replicates required for appropriate statistics. However, the device is designed for off chip automation and can be used as automated lifespan device.

As will be appreciated by those skilled in the art, other embodiments that are within the scope of the present invention can be optimized or configured for automated loading, synchronization, washing, feeding, and/or data acquisition. Moreover, the micro-pillars can be either more rigid or more deformable than described herein, as well as being decorated with colored or fluorescent stains. Furthermore, the present invention is not limited to the study of *C. elegans*.

Now referring to FIG. 1, a block diagram of microfluidic device 100 in accordance with one embodiment of the present invention is shown. The microfluidic device 100 includes a substrate 102, a cover layer 104 attached to the substrate 102 and one or more chambers 106 disposed within the cover layer 104, the substrate 102 or both. Each chamber 106 has a first end 108, a second end 110, and a set of micro-pillars 112 disposed within the chamber 106. A first microchannel 114 is disposed within the cover layer 104, the substrate 102 or both, and connected to the first end 108 of the chamber 106. A first set of barriers 116 is disposed within each first microchannel 114 proximate to the first end 108 of the chamber 106. A second microchannel 118 is disposed within the cover layer 104, the substrate 102 or both, and connected to the second end 110 of the chamber 106. A second set of barriers 120 is disposed within each second microchannel 118 proximate to the second end 110 of the chamber 106. A third microchannel 122 is disposed within the cover layer 104, the substrate 102 or both, and connected to the chamber 106. A first port 124 (e.g., buffer exchange/feeding/drug loading port) extends through the cover layer 104 and connects to the first microchannel 114. A second port 126 (e.g., buffer exchange/feeding/drug loading port) extends through the cover layer 104 and connects to the second microchannel 118. A third port 128 (e.g., worm inlet port) extends through the cover layer 104 and connects to the third microchannel 122.

The set of micro-pillars 112 form a lattice structure. As shown in Section A-A, the micro-pillars 112 are spaced apart to allow eggs and larva to be flushed from the chamber 106 and retain adult worms within the chamber 106. A height 130 of each micro-pillar 112 is less than a depth 132 of the chamber 106 such that a gap 134 is formed between each micro-pillar 112 and the substrate 102 allowing the micro-pillars 112 to be deformed by a worm to record a muscle force of the worm. The gap 134 is typically greater than or equal to an average size of an egg or an average size of a larva, and the gap 134 is less than or equal to an average size of an adult worm. For example, the height 130 of each micro-pillar 112 can be approximately 75 μm and the depth 132 of the cavity 106 can be approximately 100 μm. In one embodiment, the micro-pillars 112 have a diameter 136 of approximately 40 to 60 μm, are arranged in a lattice structure with a center to center spacing 138 of approximately 60 to 160 μm, and a ratio between an average worm body diameter to micro-pillar spacing 138 of approximately 0.68 to 2.0.

Similarly and as shown in Section B-B, the first barriers 116 and second barriers 120 are spaced apart to allow eggs and larva to be flushed from the chamber 106 and retain adult worms within the chamber 106. A height 140 of each barrier 142 in the first set of barriers 116 and the second set of barriers 120 is less than a depth 144 of the first microchannel 114 and the second microchannel 118. For example, the height 140 of each barrier 142 can be approximately 75 μm and the depth 142 of the first microchannel 114 and the second microchannel 118 can be approximately 100 μm. In one embodiment, each barrier 142 is a rectangular block with a spacing 146 of approximately 30 μm between the barriers 142.

In addition, each chamber 106 may include a fourth microchannel 148 disposed within the cover layer 104, the substrate 102 or both, and connected to the first microchannel 114 between the first set of barriers 116 and the first port 124. A fourth port 150 (e.g., air purging port) extends through the cover layer 104 and connects to the fourth microchannel 148. A fifth microchannel 152 disposed within the cover layer 104, the substrate 102 or both, and connects to the second microchannel 118 between the second set of barriers 120 and the second port 126. A fifth port 154 (e.g., air purging port) extends through the cover layer 104 and connects to the fifth microchannel 152.

Note that the microfluidic device and its features depicted in FIG. 1 are not shown to scale. Moreover, the present invention is not limited to the geometric shapes, feature sizes and feature orientations shown in FIG. 1.

Referring now to FIG. 2, a flow chart of a method 200 of making a microfluidic device having one or more chambers in accordance with one embodiment of the present invention is shown. A cover layer is formed in block 202. For each chamber, the cover layer includes a cavity with a first end and a second end, a set of micro-pillars disposed within the cavity, a first microchannel connected to the first end of the cavity, a first set of barriers disposed within the first microchannel proximate to the first end of the cavity, a second microchannel connected to the second end of the cavity, a second set of barriers disposed within the second microchannel proximate to the second end of the cavity, and a third microchannel connected to the cavity. For each chamber, a first port, a second port and a third port are formed through the cover layer in block 204. The first port is connected to the first microchannel, the second port is connected to the second microchannel, and the third port is connected to the third microchannel. The cover layer is attached to a substrate in block 206 such that each cavity forms one of the chambers, and the first microchannel, the second microchannel and the third microchannel are enclosed.

The step of forming the cover layer in block 202 may also include forming a fourth microchannel connected to the first microchannel between the first set of barriers and the first port, and a fifth microchannel connected to the second microchannel between the second set of barriers and the second port. Likewise, the step of forming the first port, the second port and the third port in block 204 may also include forming a fourth port and a fifth port through the cover layer, wherein the fourth port is connected to the fourth microchannel and the fifth port is connected to the fifth microchannel.

Figure 3:
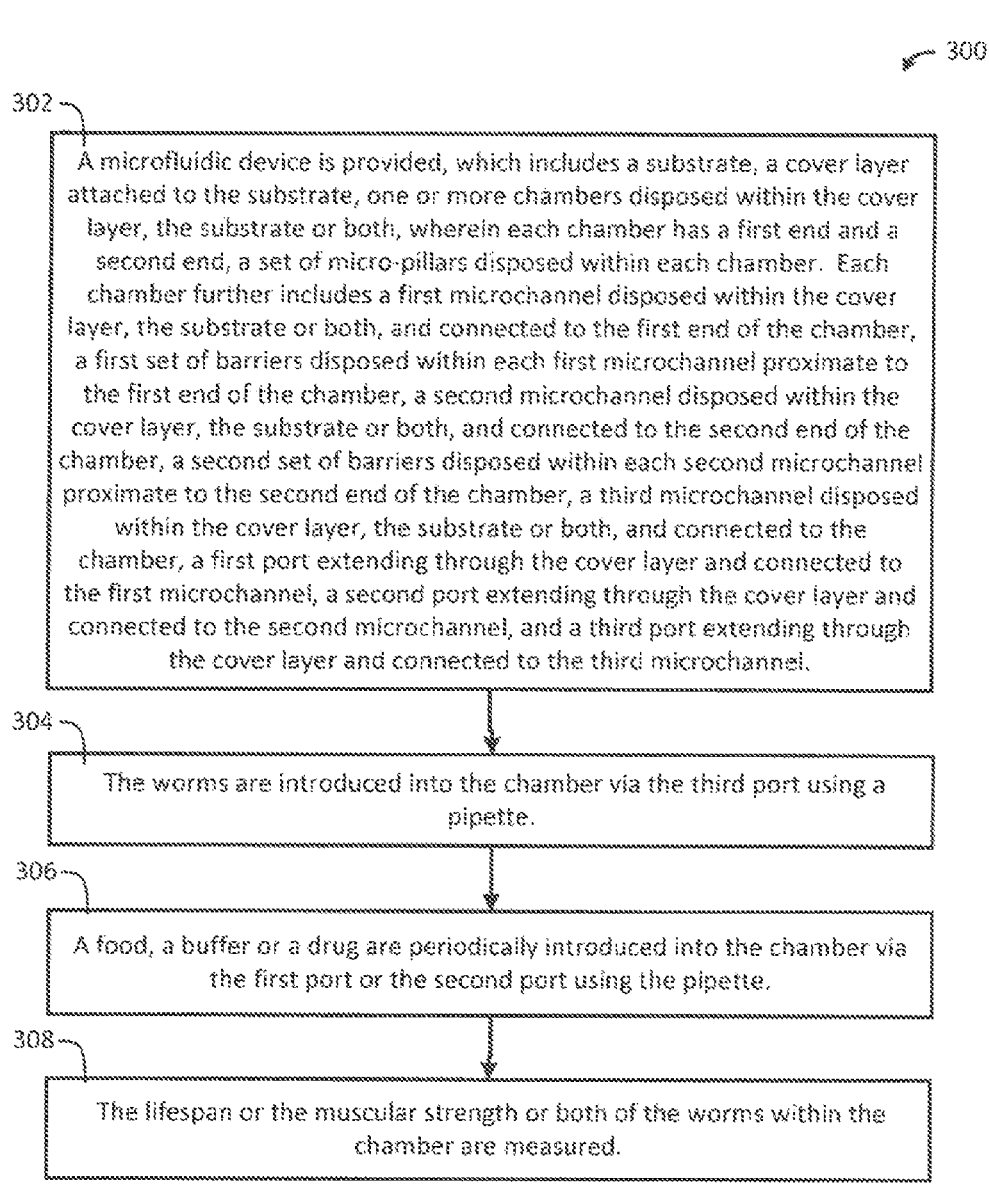
FIG. 3 is a flow chart of a method for measuring a lifespan or a muscular strength or both of worms in accordance with one embodiment of the present invention.

Now referring to FIG. 3, a flow chart of a method 300 for measuring a lifespan or a muscular strength or both of worms in accordance with one embodiment of the present invention is shown. A microfluidic device is provided in block 302, which includes a substrate, a cover layer attached to the substrate, one or more chambers disposed within the cover layer, the substrate or both, wherein each chamber has a first end and a second end, a set of micro-pillars disposed within each chamber. Each chamber further includes a first microchannel disposed within the cover layer, the substrate or both, and connected to the first end of the chamber, a first set of barriers disposed within each first microchannel proximate to the first end of the chamber, a second microchannel disposed within the cover layer, the substrate or both, and connected to the second end of the chamber, a second set of barriers disposed within each second microchannel proximate to the second end of the chamber, a third microchannel disposed within the cover layer, the substrate or both, and connected to the chamber, a first port extending through the cover layer and connected to the first microchannel, a second port extending through the cover layer and connected to the second microchannel, and a third port extending through the cover layer and connected to the third microchannel. The worms are introduced into the chamber via the third port using a pipette in block 304. A food, a buffer or a drug are periodically introduced into the chamber via the first port or the second port using the pipette in block 306. The lifespan or the muscular strength or both of the worms within the chamber are measured in block 308.

Figures 4A, 4B, 4C, 4D:
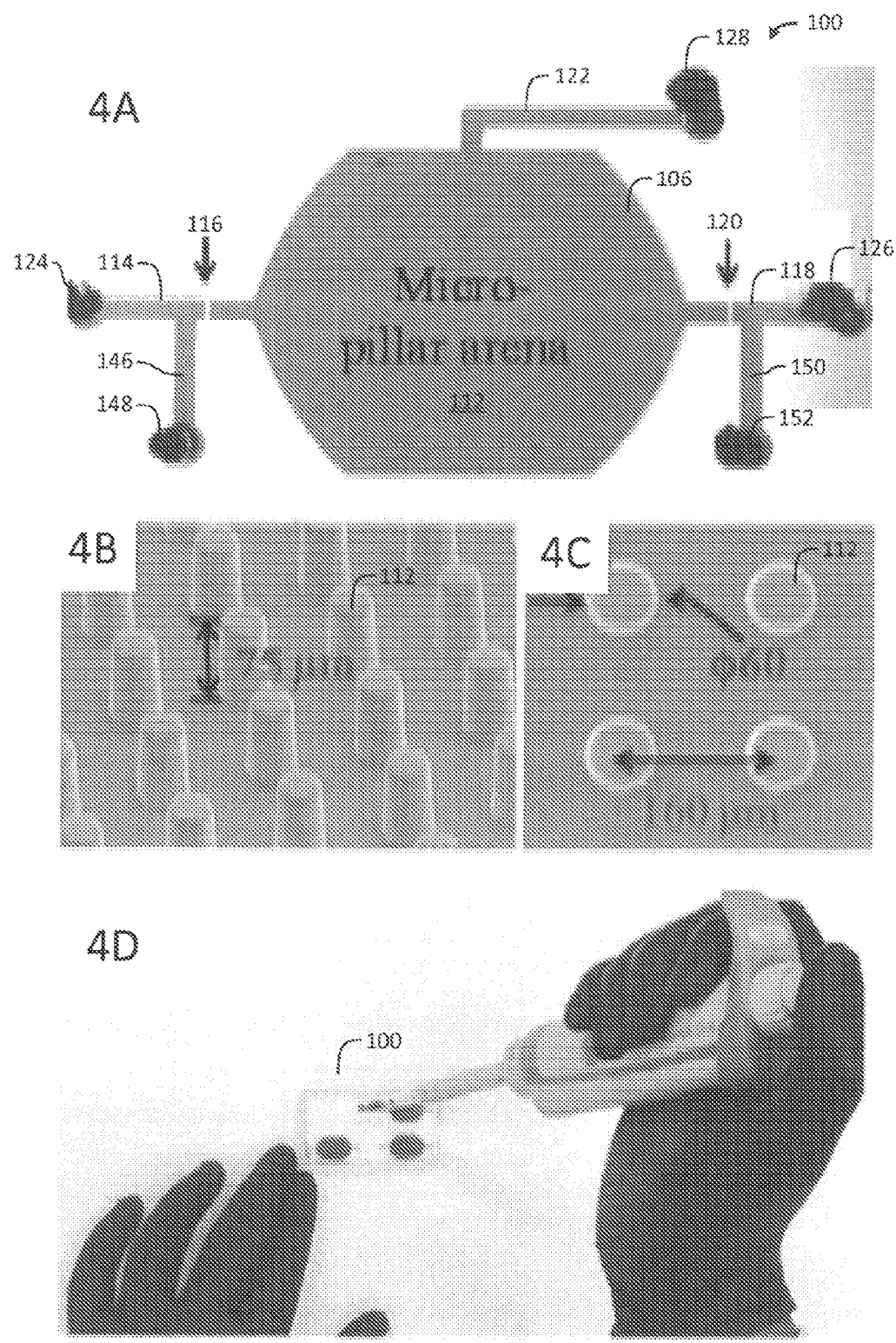
FIGS. 4A-4G illustrate a microfluidic apparatus for measuring lifespan of *C. elegans* by flow induced separation of progeny in accordance with one embodiment of the present invention.

The multifunctionality of a non-limiting example of microfluidic device in accordance with the present invention will now be demonstrated by (i) measuring lifespan curves of wild-type and long-lived mutants, (ii) recording healthspan measures such as pharyngeal pumping and locomotive parameters, (iii) conducting drug and RNAi assays, and (iv) quantifying muscle strength of animals as a function age, the latter of which has revealed insights into sarcopenia. The microfluidic apparatus used for measuring lifespan of *C. elegans* by flow induced separation of progeny is shown in FIGS. 4A-4D. FIG. 4A shows components of the apparatus and a complete view of a unit (filled with green food dye) with a worm inlet port 128, buffer exchange/feeding ports 124 and 126, air purging ports 148 and 152, and barriers for adult retention 116 and 120. A view of 75 μm tall micropillar 112 are shown in FIG. 4B, and 60 μm diameter pillars are arranged in lattice structure with 160 μm center to center spacing in FIG. 4C. FIG. 4D shows an array of transparent, portable easy to pipette microfluidic platform 100 for lifespan study (green food dye).

Worm culture: All worms have been cultured in 60 mm petri-dish on bacteria seeded nematode growth medium (NGM) at 20° C. In this study, all NGM filled petri-dishes were seeded with 200 μL of bacteria *E. Coli* OP50 and incubated for 48 hours at 20° C. This allows each plate to contain sufficient food for the worms. For synchronizing ages of the worms, approximately 50-100 gravid hermaphrodites were loaded into a lifespan chip with plenty of food. After 1 hour, the lifespan chips were washed out with M9 buffer. The wash liquid was collected and age synchronized eggs (approximately 150-200) were separated by centrifuging at 1500 rpm. Eggs were plated into the bacteria seeded plates and incubated for 60-72 hours. In this study, Wild type animals Bristol strain (N2) and two long lived mutant daf-2 (DR1564) and age-1 (hx546) were used. Wild type animals and daf-2 mutants were received from *C. elegans* genetic center (CGC) and the age-1 strain was obtained from Monica Driscoll Lab (Dept. Of Molecular Biology and Biochemistry, Rutgers, The State University of New Jersey).

Food (*E. coli* OP50) preparation: A slow growing strain of bacteria *Escherichia coli* (*E. coli* OP50) were used for the worm culture in NGM plates as well as for the lifespan study in the lifespan devices. Overnight culture of *E. coli* OP50 was used to seed the NGM plates. For all lifespan study, bacteria suspension of 100 mg/mL in S-complete solution was used which corresponds to approximately 109 bacteria/mL. 100 mg/mL bacteria suspensions were prepared by centrifuging 500 mL of overnight culture of bacteria *E. coli* OP50 of (OD=0.5) and were stored at 4° C. for subsequent use.

Worm loading/synchronization: Lifespan devices were cleaned with 70% ethanol. Before using the device for lifespan experiments, the device interior were filled with ethanol and treated for 15 minutes. All channels and interior were flushed 4/5 times with ethanol followed by S-complete solution. Age synchronized worms were washed with S-complete solution from a 72 hour NGM culture plate. Worms were cleaned by centrifuging 3 times at 1500 rpm with S-complete solution. A final worm solution of 250-400 worms/mL in S-complete solution was prepared for loading. A further dilute solution will provide better control over the number of worms/device. The lifespan device is flexible in terms of loading method and perfectly suited for pipetor, syringe/hand and syringe/pump systems. Approximately 10-15 worms were loaded into each device. Any number more than 20 worms increases the chances of starvation (qualitative observation, data not shown). Using a different syringe bacteria suspension was flowed through the device until clear S-complete solution was replaced completely. Experiments (devices were kept in 100 mm petri-dish with little DI water in it to maintain humidity) were kept at 20° C. in the incubator. Each 24 hours, worms were cleaned from their progeny (synchronization) simply by washing the device with S-complete solution (500-1000 μL). Unless stated, food was added to the experiment every day after synchronizing the worms.

Lifespan device preparation: As shown in FIGS. 4A-4D, each microfluidic device used in the study had three major components: (i) micro-pillar arena or chamber 106 where the worms will crawl, (ii) barriers 116 and 120 which prevent worms from escaping the chamber 106, and (iii) worm loading 128 and inlet/outlet ports 124 and 126. The micro-pillar chamber is 100±2.9 µm in height and is equipped with equally spaced force sensing micro-pillars in a lattice structure. As the worm grows inside a lifespan device they also grow in the ability to exert larger forces. To capturing force data from all ages of worms, micro-pillars of three different stiffness's (diameter 42±1.8, 52.03±2.1 and 61.3±1.6 µm) were used with different spacings (58, 78 and 97 µm). Each micro-pillar has one end fixed on the polydimethylsiloxane (PDMS) ceiling and is 75±3.1 µm in length which makes the other end of the micro-pillar free. This makes a clearance of 24±1.9 µm between free end of the pillar and glass floor. On each side of a lifespan device there is one channel of width 500 µm. An array of 75 µm×250 µm rectangular blocks are placed across the channel 1000 µm away from the end pillar of the micro-pillar chamber. The rectangular blocks are spaced with 30 µm between them and work as barrier to prevent the worms from escaping the chamber while bacteria, eggs and progeny can easily pass through. Channels on each side of the chamber can be used as feeding and washing ports while the other channel will be an outlet. Just before the barrier there is a purge channel on either side so that air can be purged out. On one side of the device there is a worm loading port which does not include a barrier.

All devices were prepared using soft lithography techniques. A silicone mold was fabricated by conventional photolithographic techniques on 3 inch silicon wafer (Addison Engineering, Inc.) in two steps. In the first step, a 25 µm thick pattern of only the micro-pillar arena (without any other feature) was developed using photoresist SU-8 2050 (Microchem). In the second step, a 100 µm layer pattern of the lifespan device was developed using photoresist SU-8 2100 (Microchem). The mask was aligned in such a way that the area containing the micro-pillar pattern falls exactly on top of the already developed 25 µm thick base for the pillar arena. This creates the negative for the micro-pillar of depth 75 µm while the rest of the features are of height 100 µm. A 4-6 mm thick PDMS (Sylgard 184 A and B, 1:10 by weight, Dow Corning) layer was casted into the mold and the positives were printed on the PDMS surface. All inlet/outlet holes were punched with a 1 mm whole puncher. The PDMS device was then bonded on a glass surface irreversibly and rendered as hydrophilic by plasma treatment.

Lifespan scoring assay: Worms show a reduced movement inside the chamber as they grow older especially after their reproductive stage. Worms cease movement partially or completely before they die. To score an animal dead, two stimulants are used (i) S—complete buffer solution is flowed through the device which replaces the fluid environment around the apparently dead worm and acts as mechanical stimuli similar to prodding, and (ii) tabbing the device three times with a thin metal. If there is no movement in the pharynx or in the tail 3 minutes after the stimuli has been applied, the animal is scored as dead. Each death event was scored as 1 and unaccounted (missing, washing error, matricides) was scored as 0 and Lifespan curve (Kaplan-Meier) was generated.

Locomotion assay: Both forward and backward movement was evaluated after applying tabbing stimuli. Tabbing was applied on the device with a thin metal bar. Tabbing was applied in a location just before the tip of the pharynx. As soon as the vibration reaches the inside of the device, worms induce reversal and change direction in most of the time. First and instantaneous reversal exists for a very short period (5 to 10 seconds). Only the first and instantaneous reversals were scored for reversal speed. Forward locomotion followed by the reversal was scored as forward speed.

Pharyngeal pumping: Movies of 10 individual worms were captured 15 minutes after the food addition at a rate of 20 frames/sec. Using NIH image processing software image J, the complete cycle of contraction/retraction of the isthmus/terminal bulb of pharynx were manually computed. Number of pharyngeal pumping cycles were counted over 10 second duration for each single animal and then normalized for 1 minute and reported as cycles per minute.

Results: A lifespan device should have efficient washing/feeding system and age synchronization ability. In other words, the device must have the ability of easy removal of progeny and retain the adult worms (the term "age synchronization" is used as the process of retention of adults without their progeny) inside the device. The lifespan device described in this work is optimized for hand pipetting. Washing/feeding is very easy and efficient by using a pipetor or a syringe/pump arrangement. Only 8-10 µL liquid suspensions are required to fill the entire device. Small amount of liquid handling and enclosed environment increases the ability of the lifespan device to keep the habitat sterile for long time.

Synchronization: FIGS. 4A-4D show the procedure of liquid exchange by pipetor and components of a representative device. As previously described, the device has several fluid exchange ports, barrier for retention of adults, and micropillars. The micro-pillars serve three basic purposes: (i) to age synchronize the adults based on size, (ii) help the worms to maintain crawling gait, and (iii) serve as force sensors to extract muscle force of the aging worms. Once the worm has been loaded into the device, the worm loading port is blocked with a solid pin. The worm loading port is the only exit which does not have a worm retention barrier and must be closed during feeding and flushing the progeny out. For washing the progeny out S-complete solution is flowed through the device using either of the side port. The device has approximately 25 µm clearance between the free end of the pillar and floor of the device. 75 µm tall soft and deformable micropillars are equally spaced in a lattice structure. During the reproductive stage, worms are sufficiently large in diameter (approximately 50-70 µm) that they can support the pillars by their body in all side and crawl between the pillars. At the same time, eggs are only 25-30 µm in the largest dimension and L1 larva is very tiny (15-20 µm). As a result, eggs and L1 larva's flows with the liquid between the pillar space and pillar to floor clearance. Size of the adult worm and their posture along 5-7 pillars retain them inside the device efficiently. If any worm manages to leave the pillar arena, they will be retained by the worm barrier. Worm barrier has rectangular blocks spaced 30 µm apart and makes it convenient for L1-L2 larva's flow thorough. The spacing is extremely narrow for the adult worm and retains the adult even if any worm is in the barrier region during washing/feeding.

Figures 4E, 4F, 4G:
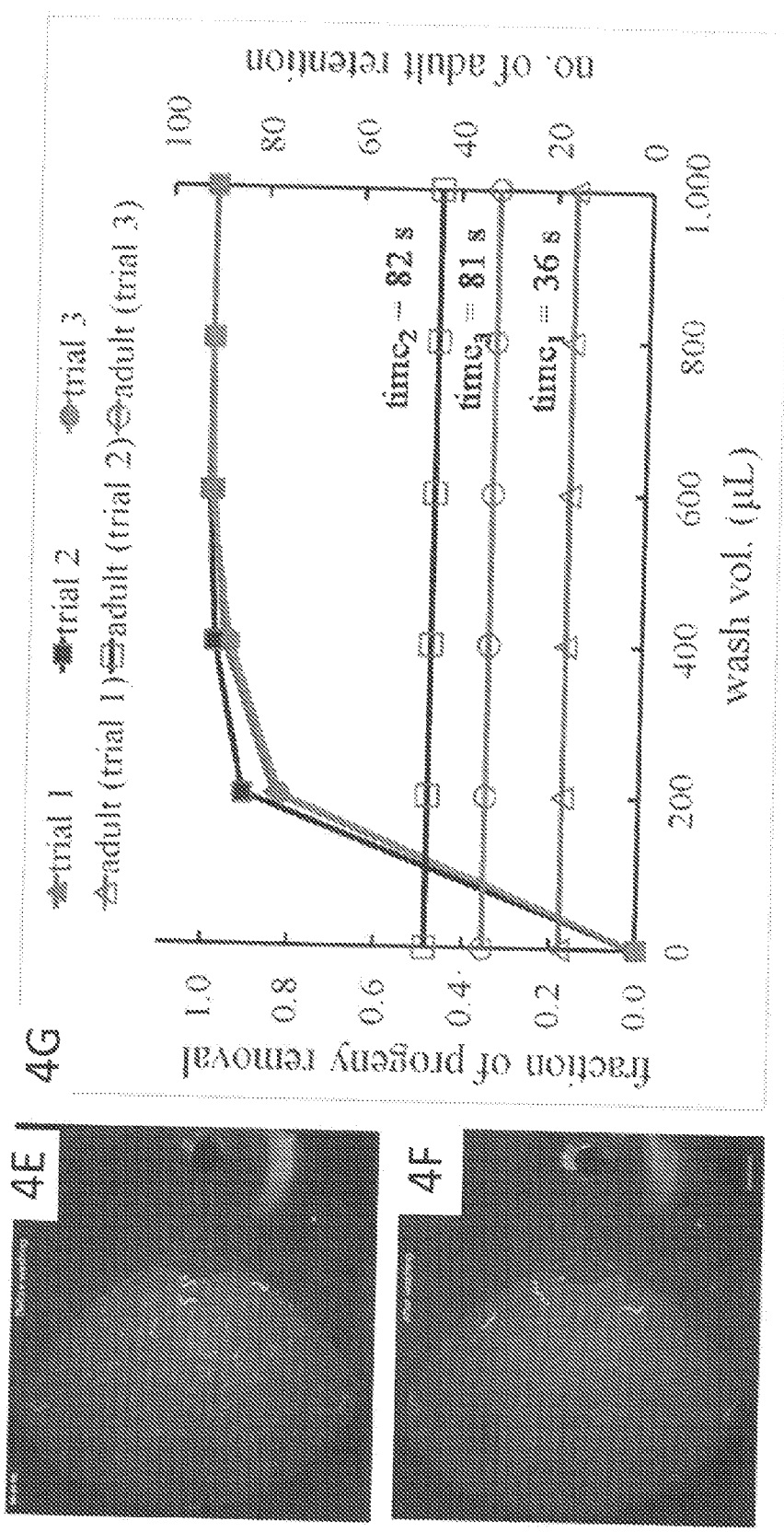

FIGS. 4E-4F represents a synchronization procedure by showing a section of a device before and after synchronization. FIG. 4E shows adult worms and their progeny in the device before inducing buffer flow through the device, and FIG. 4F shows adult worms only in the device completing the synchronization steps. Scale bar 1 mm. A little excitement was observed among the adult movement as the flow was carrying the progeny towards the outlet. In fact, during washing the adults can crawl normally. FIG. 4G is graph showing the efficiency of a representative synchronization step in terms of progeny removal and adult retention during fluid flow. In this case, three devices with 16, 32 and 44 adult worms (at the start of their reproductive stage) were washed 24 hours after loading into the device. Washing was carried out in 5 steps, each time with 200 μL of S-complete solution. Fraction of progeny removal and no of adult retention was shown against the wash volume (washing steps). During the washing study no worm was lost (the flat lines) and total removal of the progeny using less than 1 mL of buffer. Most importantly, it takes approximately 90 seconds to complete the washing, a significant improvement from lifespan study in agar plate. Open symbols and horizontal lines show complete retention of adult worms. Solid symbols correspond to the fraction progeny removal.

Figure 5A:
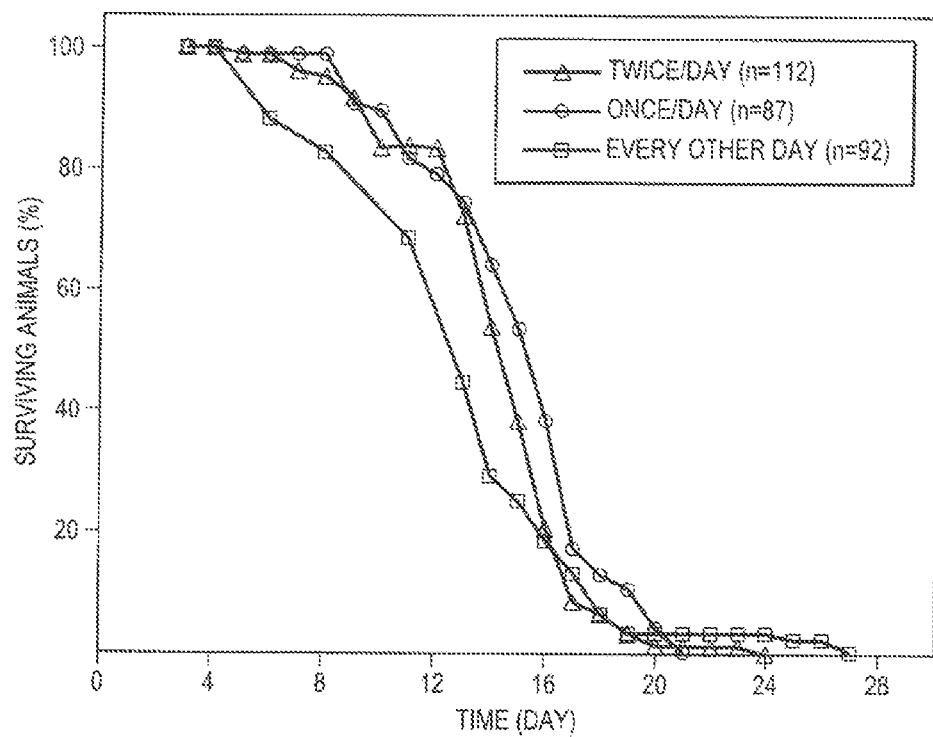
FIGS. 5A-5F illustrate optimization of feeding protocol and device geometry to achieve *C. elegans* lifespan consistent with standard assays in accordance with one embodiment of the present invention.

Development of feeding protocol for lifespan study in microfluidic lifespan device:

a. Effect of Feeding frequency and food concentration on lifespan: Dietary restriction triggers pathways for cell protection and maintenance. C. elegans also activates pathways that influences lifespan based on two factors, amount of food and frequency of food availability. Optimization of these two factors is critical for successful use of a new lifespan device. Fortunately, an E. coli OP50 bacteria suspension at 100 mg/mL was already tested as food preparation to study lifespan of C. elegans on 96 micro-titter well plate and in a microfluidic device. Three different feeding frequency were tested on this microfluidic device: (i) twice a day (n=112), (ii) once a day (n=87) and, (iii) every other day (n=92). FIG. 5A represents the lifespan of corresponding three dietary disciplines. The maximum lifespan found for the three feeding frequency is 24 days, 21 days, and 27 days with median lifespan of 15, 16, and 13 days respectively. Each pair of dietary discipline was compared based on log-rank (Mantel-Cox) test for statistical significance.

Figure 5B:
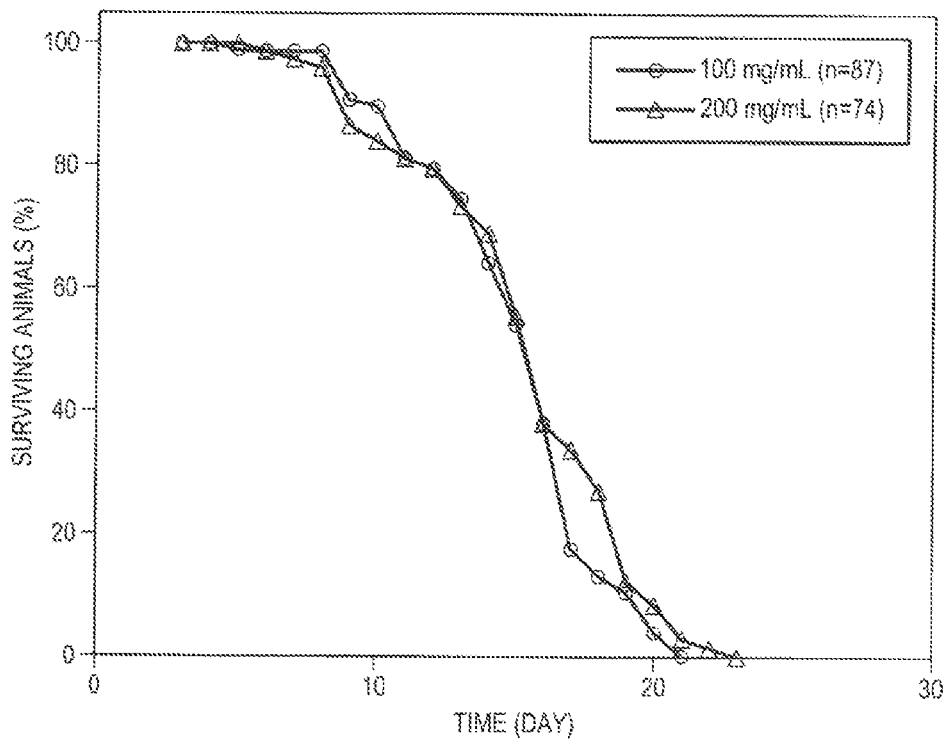
Figure 5C:
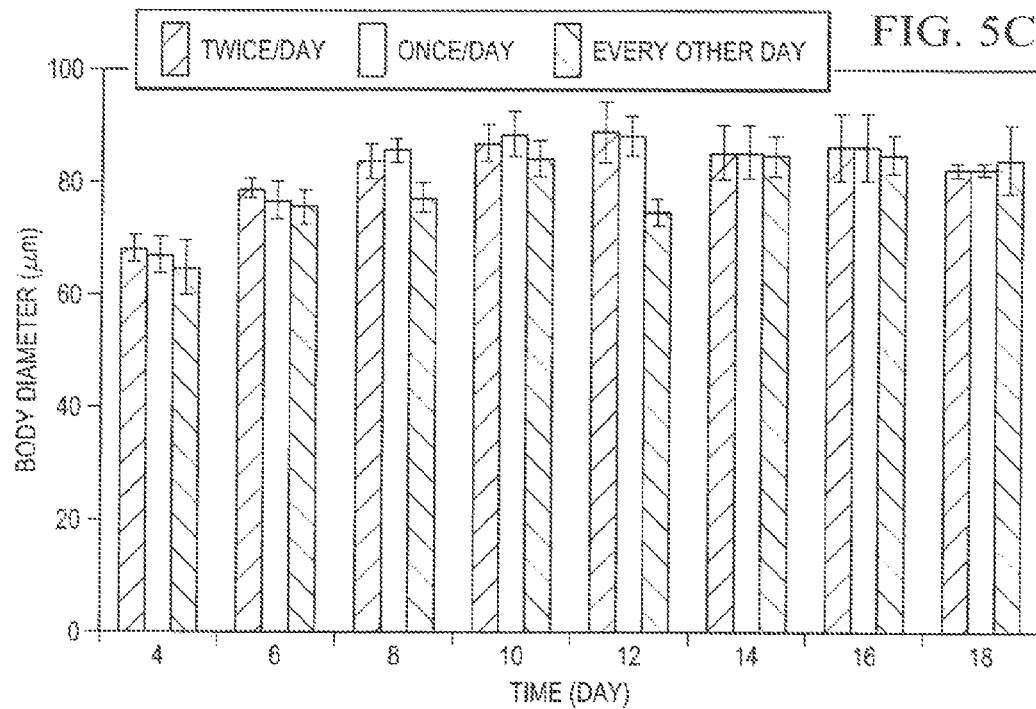
Figure 5D:
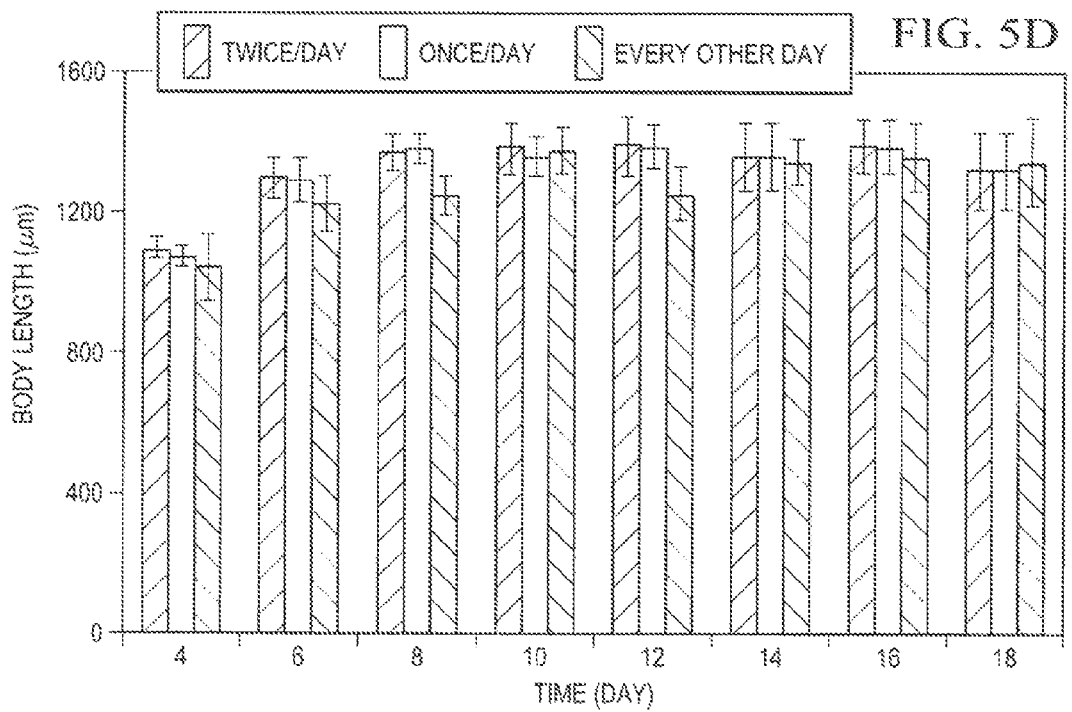

Apparently, feeding regulation 100 mg/mL every other day seems to induce dietary restriction in some animals and shows an increase in maximum lifespan (27 days). Lifespan curve for feeding frequency of every other day is significantly different (p-value=0.0036) compared to other dietary discipline. Worms treated with feeding regulation of twice a day (100 mg/mL) are not suffering from starvation and follows similar lifespan curve for well fed animal in agar plate. Lifespan for worms from feeding regulation of once per day (100 mg/mL) is different (p-value=0.0244) from feeding regulation of twice a day (100 mg/mL). To confirm, the lean possibility of chronic food limitation with feeding 100 mg/mL bacteria once every day, another lifespan assay was carried out with 200 mg/mL bacteria once/day once. FIG. 5B shows a median lifespan for animal treated with feeding of 200 mg/mL and once a day is 16 days (max. lifespan 23 days). A statistically similar result (p-value=0.208) with 100 mg/mL and once per day indicates, feeding regulation 200 mg/mL, once/day, 100 mg/mL, once/day and 100 mg/mL, twice/day provides sufficient food to prevent starvation. As per the above analysis, 100 mg/mL and once per day is a suitable diet and believed to be optimum for lifespan study in fluidic environment. It is also suitable for operational simplicity. However, growth of the worm in terms of the body length and body girth was monitored over the course of their life to find the best diet for fluidic environment.

b. growth of worm under different dietary regulation: During the period of developing feeding protocol, we also observed the development of the worms in terms of their body diameter and length. Well fed wild type worms of age 60 hours grow approximately 48.5±2.3 μm in body diameter and by the time they entered their reproductive stage it is between 65 to 70 μm. All animals loaded into the lifespan device were at their early reproductive stage. From FIGS. 5C and 5D, it is evident that both body diameter and length continue to grow to the end of their reproductive stage (day 10). After the reproductive stage is over, body diameter and lengths largely remain the same. Shrinkage of the body diameter of approximately 9-12% was observed and a little change in the length was observed for feeding regulation of once per day and twice per day. These observations are consistent with the animals studied on agar plate. The changes on body diameter and length are not consistent for the worms of dietary regulation of every other day with the worms grown on agar plate.

Figure 5E:
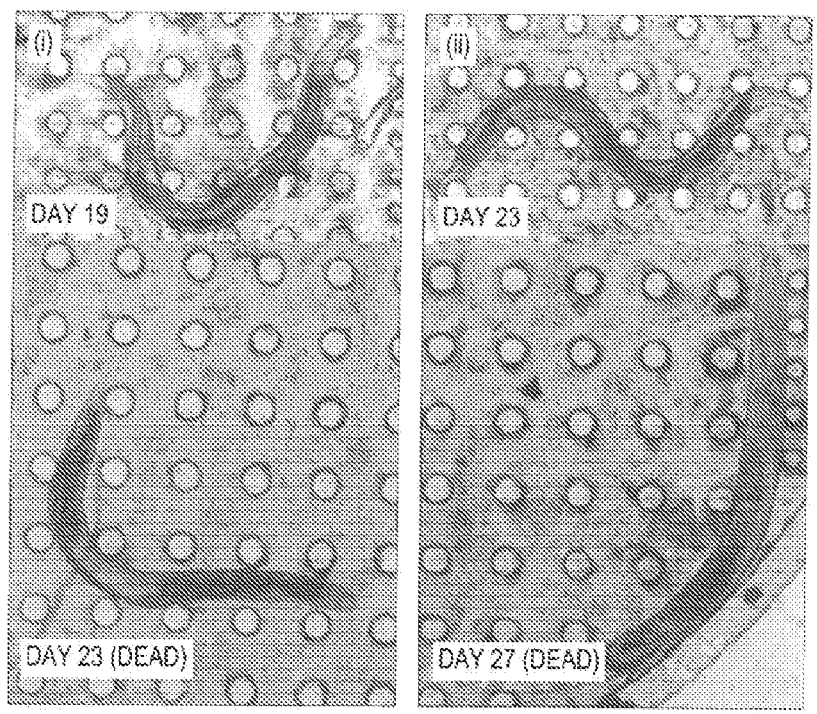

Several events of worm death have been recorded and are shown in FIG. 5E. Usually, buffer fluid is flowed around the worm body and look for shuttle movement for animal pharynx before declaring the animal dead. In almost all cases, shrinkage in the body diameter and length was observed. Dead worms tend to be rod like when they are dead and align between rows of pillars most often straight or curved as arc. Even if the body bends of a dead worm upon flow of fluid it quickly becomes straight when flow is withdrawn. Once the animal is dead, the dark interior becomes pale in subsequent days (approximately 3rd day) body sometimes breaks into pieces (disintegrates).

Optimization of pillar spacing for the aging device: Diameter and spacing of the pillars were optimized to match the agar crawling gait and to extract muscular force of the growing worm. Material property of the pillars, imaging limitation and maximum muscular strength of the worm dictates pillar diameter. Regularly spaced micro-pillars help worms to crawl in a fluidic environment and the spacing of the pillars dictates wavelength, amplitude and frequency of crawling worms. A ratio (Rs) between worm average body diameter (d) of worms to pillar spacing (s) were used to define the spacing. Devices of three different spacing to diameter ratio (Rs: 1.21, 1.2, and 1.15 for spacing≈60 μm, 80 μm, and 100 μm) were used to optimize the pillar spacing. This ratio continuously changes as the worms continue to grow. It falls below 1 if worm diameter exceeds pillar spacing meaning a confinement for worms. Crawling of worms was characterized in terms of wavelength and amplitude in all three devices. A four day old adult worm exhibit wavelength of 607±53.4 μm as compared to 650±40 μm during crawling. Micro-pillars arranged in lattice structure are a closer match to the soil environment, at least in terms of locomotory behavior. It will stimulate the sensory neurons and the muscles in a similar way as their natural habitat. Also, pillar support reduces slip and makes crawling efficient. As it will be always in a liquid environment, it will not feel the pinning effect. Thus, the worm will face a stress level that closely matches to its natural environment.

Figure 5F:
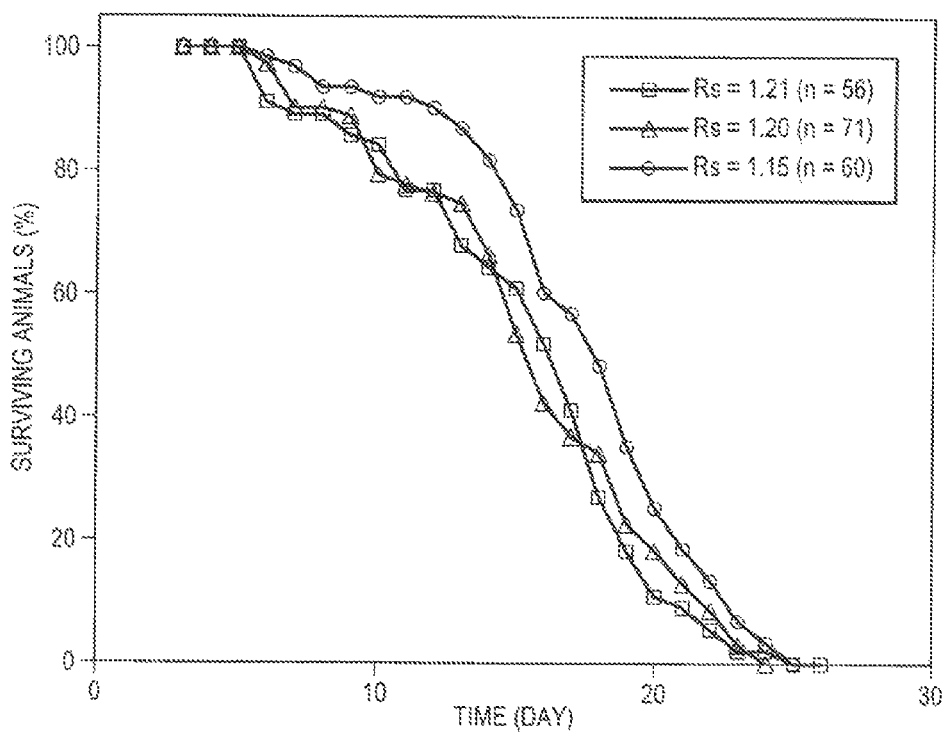

FIG. 5F shows the lifespan curves for wild type animal in each of these devices characterized by the ratio Rs. The range of values for Rs is shown in the figure. There is no significant difference in terms of the total/maximum lifespan. Each device is capable to reproduce lifespan of wild type animals with little differences. Devices (i) and (ii) where Rs drops below 1 at some point along the lifespan are 16 and 15 days respectively. Interestingly, device (iii) which keeps Rs always above 1 through the lifespan shows a better median lifespan of 17 days. In device (iii), there is much freedom to make turns and moves as compared to the other two devices, at least when the animals are grown up. Device (i) and (ii) introduces default deflection of the pillar when Rs falls below 1, these two types of devices are not suitable for extracting muscular forces after certain ages of the animals. Based on the crawling behavior, lifespan of the worms and ability to extract muscular forces, device (iii) were used for subsequent lifespan study in fluidic pillar devices.

Figure 6A:
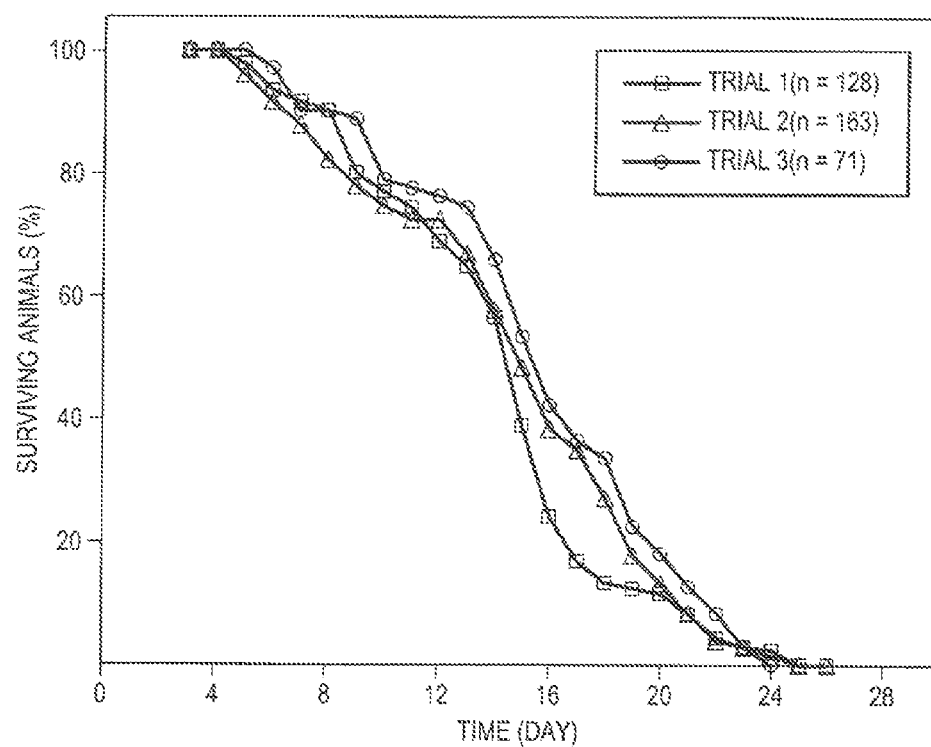
FIGS. 6A-6C illustrate a lifespan study of *C. elegans* and its age mutants in the microfluidic device in accordance with one embodiment of the present invention.
Figure 6B:
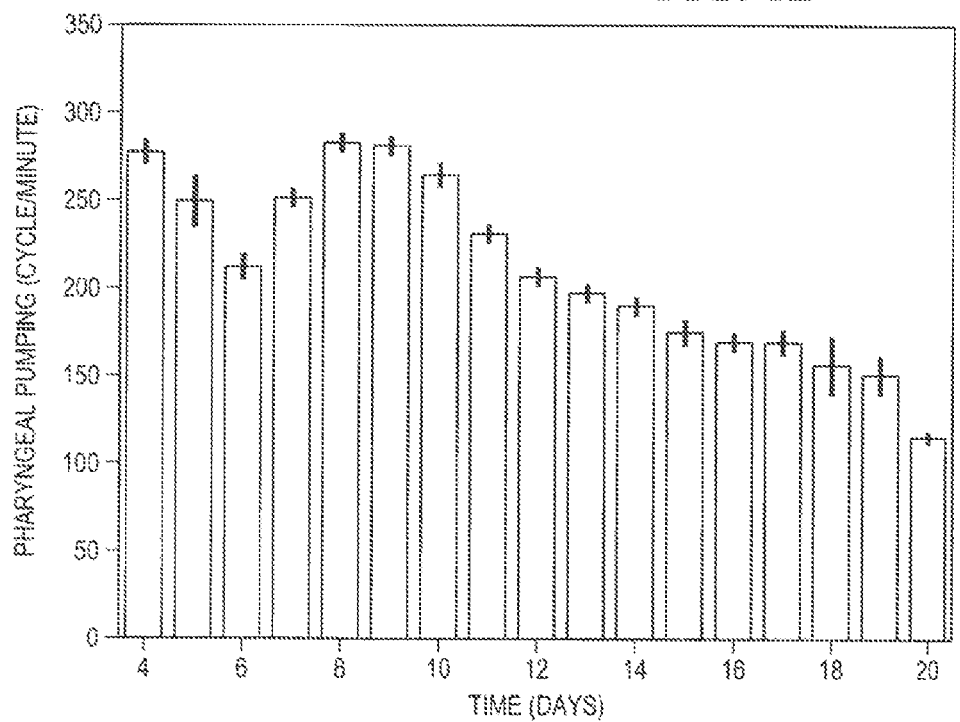
Figure 6C:
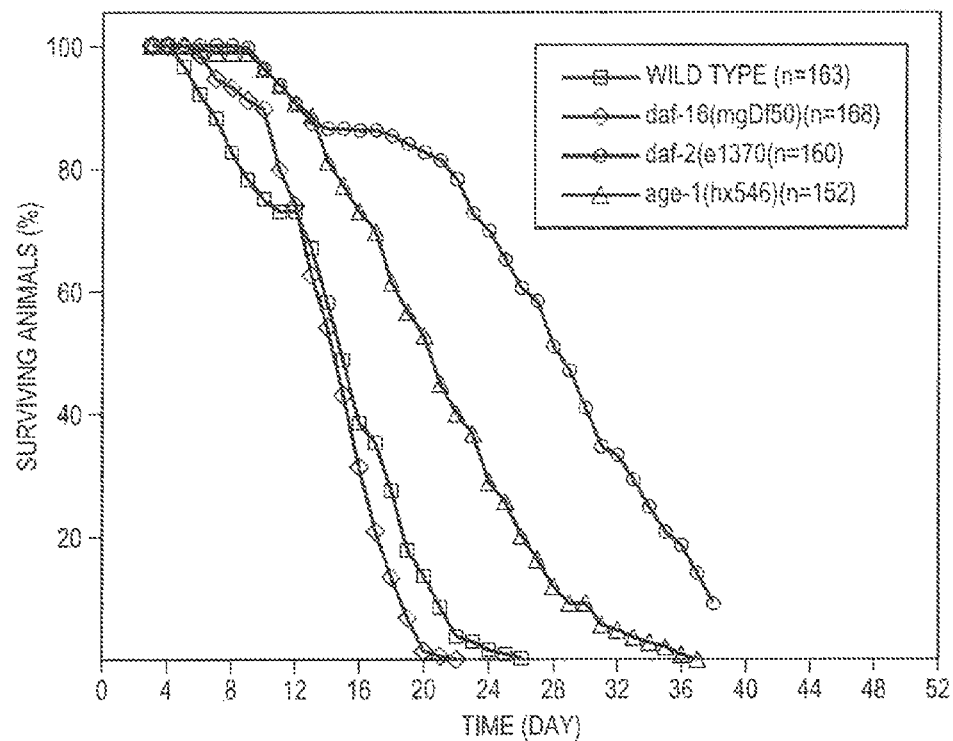

Lifespan study of age mutants in optimized lifespan device: Lifespan study was carried out for wild type and three of its age mutant daf-2(e1307), daf-16(mgDf50), and age-1(hx546) using the optimized lifespan device. FIGS. 6A-C represents the ability of the microfluidic lifespan device for carrying out the lifespan study with genetic modification that extends lifespan. FIG. 6A shows the reproducibility of the lifespan curve for wild type animals (N=3). Median lifespan of wild type C. elegans (N=3) is found to be 17, 14 and 15 with maximum lifespan of 24, 25 and 25 which agrees most of the lifespan study from classical agar based experiment. FIG. 6A also confirms the high degree of reproducibility of lifespan data using the fluidic lifespan device. FIG. 6C represents the lifespan of C. elegans age mutants. Wild type and age mutant daf-16, age-1 and daf-2 have median lifespan of 16, 15, 21, and 29 days respectively which matches the similar lifespan extension (shorten for daf-16, $\approx$1.5 times increase for age-1 and $\approx$2.1 times increase for daf-2 compared to wild type) found in agar study. These mutants have maximum lifespan of 22, 25, 36 and 44 days respectively. This suggests that the device is capable of keeping the environment sterile long enough to run the lifespan study for genetic modifications. Along with the lifespan study, movies were also captured and pharyngeal pumping was scored every day for 10 crawling worms.

C. elegans uses rhythmic contraction/relaxation of pharynx (pharyngeal pumping) to intake bacteria from liquid suspension. Pharyngeal pumping of wild type animals normally depends on number of factors, such as (i) availability of food, (ii) quality of food, and (iii) condition of the environment. Normally, in liquid suspension well-fed worm's pumps pharynx in the presence of bacteria and starved worms keep pumping slowly and irregularly. Starved worms accelerate pumping in the presence of lower amount of bacteria compared to well-fed worms. However, well-fed worm exhibits a gradual decrease in the pharyngeal pumping with aging which makes it an attractive physiological parameter for aging. Pharyngeal pumping for wild type animals were scored at least 30 minutes after washing and feeding the worm in the device. This ensures the quality and availability of food with proper concentration. FIG. 6B shows the changes of pharyngeal pumping of a population of wild type C. elegans. Pharyngeal pumping increases during the reproductive stage ends (maximum $\approx$283 cycle/minute on day 8). It decreases gradually starting from day 10 to the end (minimum $\approx$117 cycle/minute on day 20). After day 20, the pharynx of aged worms shrinks and the body darkens which makes counting very difficult. Pharyngeal pumping rate decreases much slowly compared to the worms grown in agar. In agar plate, worm crawls on the bacterial lawn which means concentrated bacteria source. In fluidic environment, bacteria suspend on liquid and worms must pump regularly to intake sufficient amount of bacteria required for maintaining normal metabolism after the reproductive stage. This makes the worm having much higher pumping rate even before dying. High pumping rate in fluidic environment may have advantages for drug treatment.

Reversal is a good mobility indicator for aging: Reversal is an important locomotive character of C. elegans. Worm uses reversal to avoid danger and the first reversal is a means of immediate avoidance followed by reversal for direction change. An increase in the numbers of reversals in worm locomotion with age is also reported. Since, its reversal is a means to avoid lethal situation, reversal must be spontaneous and speed of reversal could be a very good indicator for muscular aging. In an effort to connect mobility as an indicator of muscular aging, both forward mobility speed and reversal speed were calculated. From day 4 to 10 animals were showing reversal by themselves, after day 14 all reversals were induced by a mechanical stimulus (gentle tabbing on the device 3 times). The episode for evaluating reversal speed was chosen carefully from device (iii) with pillar spacing to worm diameter ratio greater than 1. Continuous frames of a spontaneous start of reversal and end of reversal were taken as a reversal episode. Reversal episodes with pause or stop or intermittent reversal were not included. An NIH image processing software image J were used to evaluate the speed from the images.

Figure 7A:
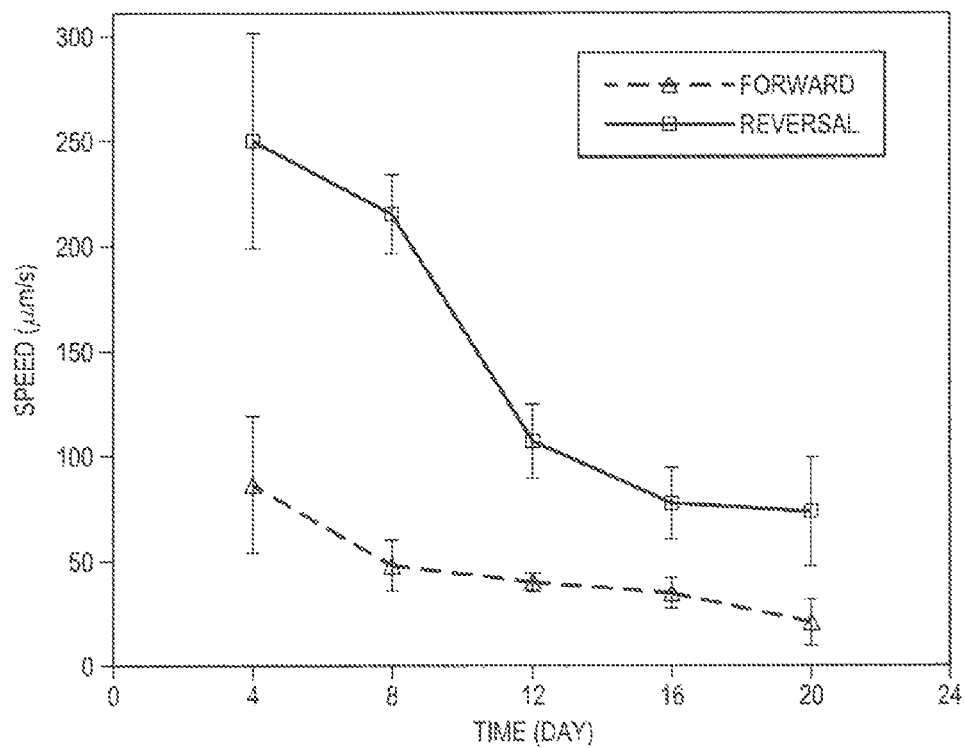
FIG. 7A is a graph showing locomotive speed of forward movement and 1st reversal of crawling wild type *C. elegans* population as a function of age of aging in accordance with one embodiment of the present invention.
Figure 7B:
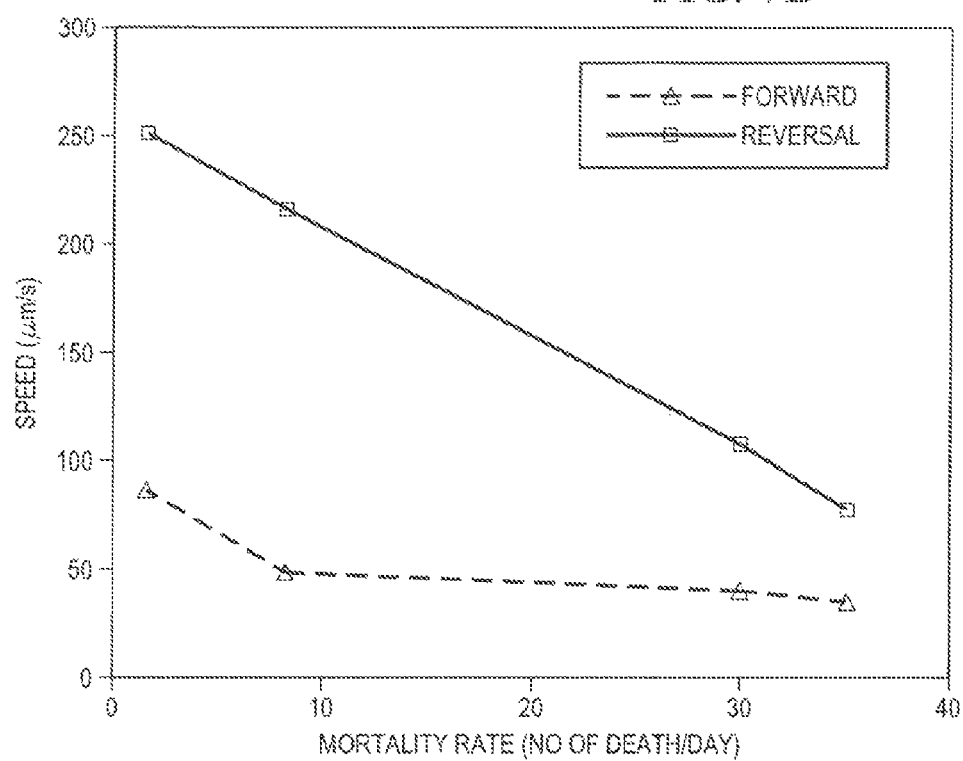
FIG. 7B is a graph showing a correlation between the locomotive speed [forward and reversal] and animal mortality rate in accordance with one embodiment of the present invention.
Figure 7C:
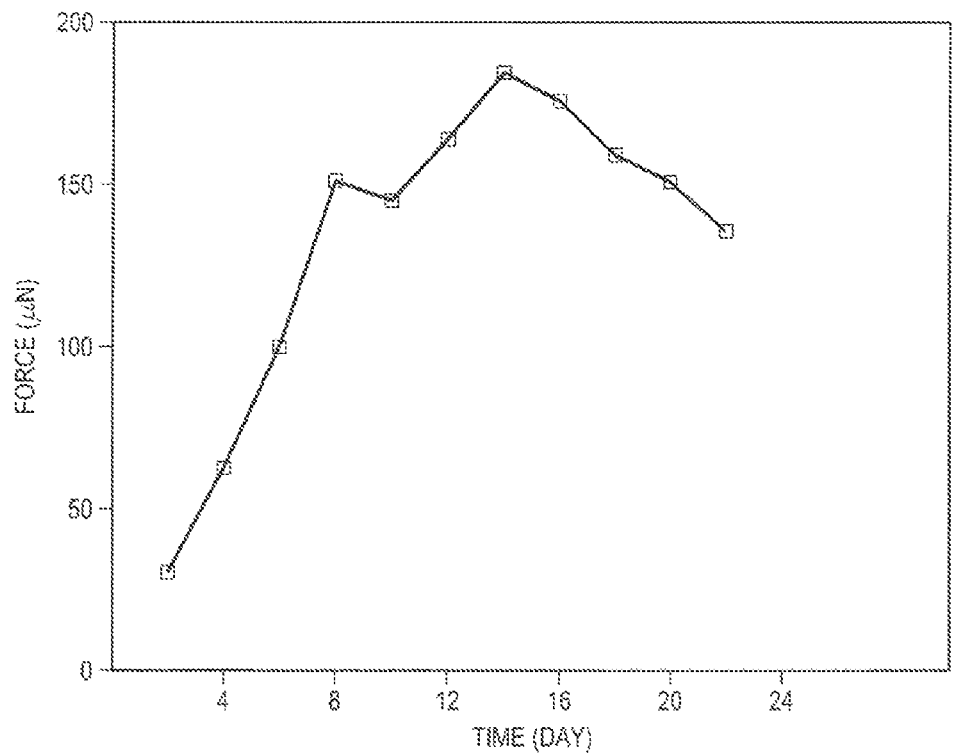
FIG. 7C shows the muscular strength increase during development and subsequent decline as the animal ages in accordance with one embodiment of the present invention.

FIG. 7A shows the variation of both forward and reverse movement over the age of an animal population. Reversal is always associated with greater speed and the decline in reversal speed is much sharper and noticeable. Most importantly, the rate of decline in reversal speed is much sharper near the end of the reproductive stage and specifically after day 8. This observation suggests, initiation of muscular aging is picked up by the reversal speed of worms even if the muscular aging is stochastic in nature. In other words, reversal speed is sensitive to stochastic nature of aging. FIG. 7B supports strongly to the above mentioned observation as sharp increase in the mortality rate is initiated by the sharp decline in the reversal speed. FIG. 7C shows the muscular strength increase during development and subsequent decline as the animal ages. FIG. 8 shows tables for lifespan study (development of feeding protocol, spacing trials, reproducibility of lifespan for the wild type animal in optimized device with optimized diet, and lifespan for age mutants). FIG. 9 is a table showing a characterization of crawling behavior of worms in fluidic micropillar arena.

A microfluidic tool for phenotyping (neuro)muscular strength in C. elegans: To make C. elegans a comprehensive genetic model for muscle health investigations, the microfluidic device (NemaFlex) contains deformable pillars for quantifying muscle strength in C. elegans. Animals crawl through the pillars pushing them, allowing extraction of local forces from pillar displacements. Since the forces fluctuate depending on animal's behavior, velocity, body shape and position with respect to pillar, quantitation of animal strength has thus far remained elusive. Driven by the need to anchor NemaFlex for high throughput muscle strength assays, a robust experimental protocol and analysis workflow was developed to sample the full range of forces and define a metric for maximum strength. NemaFlex was also configured for recording strength across virtually the entire lifespan of animals permitting sarcopenia investigations. FIG. 7C shows the muscular strength increase during development and subsequent decline as the animal ages.

It was found that animals subjected to muscle contractions with an acetylcholine agonist, prior to paralysis show the same maximum strength as the untreated animals suggesting NemaFlex quantitates maximum strength. Mutants with neuronal defects (unc-17 and unc-119) and impaired sarcomeres (unc-52 and unc-112) were tested and changes indicating the neuromuscular origin of strength were observed. Muscle strength across the lifespan of a wild-type population was profiled, and the results show that muscle strength increases 7-fold from day-2 to day-14 followed by a sharp decline—providing the first direct evidence of muscle strength loss due to sarcopenia. In summary, NemaFlex is a powerful tool to conduct prospective life-long investigations of muscle strength in C. elegans and mutants.

The foregoing description of the apparatus and methods of the invention in preferred and alternative embodiments and variations, and the foregoing examples of processes for which the invention may be beneficially used, are intended to be illustrative and not for purpose of limitation. The invention is susceptible to still further variations and alternative embodiments within the full scope of the invention, recited in the following claims.

The invention claimed is:

1. A microfluidic device comprising:
a substrate;
a cover layer attached to the substrate;
one or more chambers disposed within the cover layer, the substrate or both, wherein each chamber has a first end and a second end;
a set of micro-pillars disposed within each chamber and extending downward from the cover layer, wherein a height of each micro-pillar is less than a depth of the chamber such that a gap is formed between a bottom of each micro-pillar and the substrate; and
for each chamber:
a first microchannel disposed within the cover layer, the substrate or both, and connected to the first end of the chamber,
a first set of barriers disposed within each first microchannel proximate to the first end of the chamber and extending downward from the cover layer, wherein a height of each barrier in the first set of barriers is less than a depth of the first microchannel such that a first barrier gap is formed between a bottom of each barrier in the first set of barriers and the substrate,
a second microchannel disposed within the cover layer, the substrate or both, and connected to the second end of the chamber,
a second set of barriers disposed within each second microchannel proximate to the second end of the chamber and extending downward from the cover layer, wherein a height of each barrier in the second set of barriers is less than a depth of the second microchannel such that a second barrier gap is formed between a bottom of each barrier in the second set of barriers and the substrate,
a third microchannel disposed within the cover layer, the substrate or both, and connected to the chamber,
a first port extending through the cover layer and connected to the first microchannel,
a second port extending through the cover layer and connected to the second microchannel, and
a third port extending through the cover layer and connected to the third microchannel.

2. The microfluidic device as recited in claim 1, wherein the set of micro-pillars form a lattice structure.

3. The microfluidic device as recited in claim 1, wherein the micro-pillars are spaced apart to allow eggs and larva to be flushed from the chamber and retain adult worms within the chamber.

4. The microfluidic device as recited in claim 1, wherein the gap allows the micro-pillars to be deformed by a worm to record a muscle force of the worm.

5. The microfluidic device as recited in claim 1, wherein the gap is greater than or equal to an average size of an egg or an average size of a larva, and the gap is less than or equal to an average size of an adult worm.

6. The microfluidic device as recited in claim 1, wherein the height of each micro-pillar is approximately 75 µm and the depth of the cavity is approximately 100 µm.

7. The microfluidic device as recited in claim 1, wherein the micro-pillars have a diameter of approximately 40 to 60 µm, are arranged in a lattice structure with a center to center spacing of approximately 60 to 160 µm, and a ratio between an average worm body diameter to micro-pillar spacing of approximately 0.68 to 2.0.

8. The microfluidic device as recited in claim 1, wherein the first barriers and second barriers are spaced apart to allow eggs and larva to be flushed from the chamber and retain adult worms within the chamber.

9. The microfluidic device as recited in claim 1, wherein the height of each barrier is approximately 75 µm and the depth of the first microchannel and the second microchannel are approximately 100 µm.

10. The microfluidic device as recited in claim 1, wherein each barrier in the first set of barriers and the second set of barriers comprises a rectangular block.

11. The microfluidic device as recited in claim 1, wherein the barriers in the first set of barriers and the second set of barriers are spaced apart by approximately 30 µm.

12. The microfluidic device as recited in claim 1, wherein:
the first port comprises a first buffer exchange/feeding/drug loading port;
the second port comprises a second buffer exchange/feeding/drug loading port; and
the third port comprises a worm inlet port.

13. The microfluidic device as recited in claim 1, further comprising for each chamber:
a fourth microchannel disposed within the cover layer, the substrate or both, and connected to the first microchannel between the first set of barriers and the first port;
a fourth port extending through the cover layer and connected to the fourth microchannel;
a fifth microchannel disposed within the cover layer, the substrate or both, and connected to the second microchannel between the second set of barriers and the second port; and
a fifth port extending through the cover layer and connected to the fifth microchannel.

14. The microfluidic device as recited in claim 13, wherein:
the fourth port comprises a first air purging port; and
the fifth port comprises a second air purging port.

15. A method of making a microfluidic device having one or more chambers comprising:
forming a cover layer having, for each chamber, a cavity with a first end and a second end, a set of micro-pillars disposed within the cavity and extending downward from the cover layer, a first microchannel connected to the first end of the cavity, a first set of barriers disposed within the first microchannel proximate to the first end of the cavity and extending downward from the cover layer, a second microchannel connected to the second end of the cavity, a second set of barriers disposed within the second microchannel proximate to the second end of the cavity and extending downward from the cover layer, and a third microchannel connected to the cavity, wherein a height of each micro-pillar is less than a depth of the chamber such that a gap is formed between a bottom of each micro-pillar and the substrate, a height of each barrier in the first set of barriers is less than a depth of the first microchannel such that a first barrier gap is formed between a bottom of each barrier in the first set of barriers and the substrate, and a height of each barrier in the second set of barriers is less than a depth of the second microchannel such that a second barrier gap is formed between a bottom of each barrier in the second set of barriers and the substrate;

forming, for each chamber, a first port, a second port and a third port through the cover layer, wherein the first port is connected to the first microchannel, the second port is connected to the second microchannel, and the third port is connected to the third microchannel; and attaching the cover layer to a substrate such that each cavity forms one of the chambers, and the first microchannel, the second microchannel and the third microchannel are enclosed.

16. The method as recited in claim 15, wherein the set of micro-pillars form a lattice structure.

17. The method as recited in claim 15, wherein the micro-pillars are spaced apart to allow eggs and larva to be flushed from the chamber and retain adult worms within the chamber.

18. The method as recited in claim 15, wherein the gap allows the micro-pillars to be deformed by a worm to record a muscle force of the worm.

19. The method as recited in claim 15, wherein the gap is greater than or equal to an average size of an egg or an average size of a larva, and the gap is less than or equal to an average size of an adult worm.

20. The method as recited in claim 15, wherein the height of each micro-pillar is approximately 75 µm and the depth of the cavity is approximately 100 µm.

21. The method as recited in claim 15, wherein the micro-pillars have a diameter of approximately 40 to 60 µm, are arranged in a lattice structure with a center to center spacing of approximately 60 to 160 µm, and a ratio between an average worm body diameter to micro-pillar spacing of approximately 0.68 to 2.0.

22. The method as recited in claim 15, wherein the first barriers and second barriers are spaced apart to allow eggs and larva to be flushed from the chamber and retain adult worms within the chamber.

23. The method as recited in claim 15, wherein a height of each barrier in the first set of barriers and the second set of barriers is less than a depth of the first microchannel and the second microchannel.

24. The method as recited in claim 23, wherein the height of each barrier is approximately 75 µm and the depth of the first microchannel and the second microchannel are approximately 100 µm.

25. The method as recited in claim 23, wherein each barrier in the first set of barriers and the second set of barriers comprises a rectangular block.

26. The method as recited in claim 23, wherein the barriers in the first set of barriers and the second set of barriers are spaced apart by approximately 30 µm.

27. The microfluidic device as recited in claim 15, wherein:
the first port comprises a first buffer exchange/feeding/drug loading port;
the second port comprises a second buffer exchange/feeding/drug loading port; and
the third port comprises a worm inlet port.

28. The method as recited in claim 15, wherein:
the step of forming the cover layer further comprises forming a fourth microchannel connected to the first microchannel between the first set of barriers and the first port, and a fifth microchannel connected to the second microchannel between the second set of barriers and the second port; and
the step of forming the first port, the second port and the third port further comprises forming a fourth port and a fifth port through the cover layer, wherein the fourth port is connected to the fourth microchannel and the fifth port is connected to the fifth microchannel.

29. The method as recited in claim 28, wherein:
the fourth port comprises a first air purging port; and
the fifth port comprises a second air purging port.

30. A method for measuring a lifespan or a muscular strength or both of worms comprising:
providing a microfluidic device comprising a substrate, a cover layer attached to the substrate, one or more chambers disposed within the cover layer, the substrate or both, wherein each chamber has a first end and a second end, a set of micro-pillars disposed within each chamber and extending downward from the cover layer, wherein a height of each micro-pillar is less than a depth of the chamber such that a gap is formed between a bottom of each micro-pillar and the substrate, and for each chamber:
a first microchannel disposed within the cover layer, the substrate or both, and connected to the first end of the chamber,
a first set of barriers disposed within each first microchannel proximate to the first end of the chamber and extending downward from the cover layer, wherein a height of each barrier in the first set of barriers is less than a depth of the first microchannel such that a first barrier gap is formed between a bottom of each barrier in the first set of barriers and the substrate,
a second microchannel disposed within the cover layer, the substrate or both, and connected to the second end of the chamber,
a second set of barriers disposed within each second microchannel proximate to the second end of the chamber and extending downward from the cover layer, wherein a height of each barrier in the second set of barriers is less than a depth of the second microchannel such that a second barrier gap is formed between a bottom of each barrier in the second set of barriers and the substrate,
wherein the gap, the first barrier gap and the second barrier gap are configured to allow eggs and larva to be flushed from the chamber and retain adult worms within the chamber,
a third microchannel disposed within the cover layer, the substrate or both, and connected to the chamber,
a first port extending through the cover layer and connected to the first microchannel,
a second port extending through the cover layer and connected to the second microchannel, and
a third port extending through the cover layer and connected to the third microchannel;
introducing the worms into the chamber via the third port using a pipette;
periodically delivering a food, a buffer or a drug into the chamber via the first port or the second port using the pipette;
periodically flushing eggs and larva from the chamber using the first port or the second port; and
measuring the lifespan or the muscular strength or both of the worms within the chamber.

31. The microfluidic device as recited in claim 1, wherein the gap, the first barrier gap and the second barrier gap are configured to allow eggs and larva to be flushed from the chamber and retain adult worms within the chamber.

32. The method as recited in claim 15, wherein the gap, the first barrier gap and the second barrier gap are configured to allow eggs and larva to be flushed from the chamber and retain adult worms within the chamber.

* * * * *